United States Patent [19]

Atkinson

[11] Patent Number: 5,215,532
[45] Date of Patent: Jun. 1, 1993

[54] CATHETER DEVICE WITH EASILY DEPLOYED RETAINER

[76] Inventor: Meredith C. Atkinson, P.O. Box 1206, Siloam Springs, Ark. 72761

[21] Appl. No.: 675,436

[22] Filed: Mar. 26, 1991

[51] Int. Cl.$^5$ .............................................. A61M 5/32
[52] U.S. Cl. ............................. 604/180; 128/DIG. 26
[58] Field of Search ................ 604/164, 174, 177–180; 128/DIG. 26; 602/54, 903

[56] References Cited

U.S. PATENT DOCUMENTS

| | | | |
|---|---|---|---|
| 2,727,512 | 12/1955 | Muller | 128/DIG. 26 |
| 3,146,778 | 9/1964 | Krawiec | 604/180 |
| 3,826,254 | 7/1974 | Mellor | 604/180 |
| 4,057,066 | 11/1977 | Taylor | 128/349 |
| 4,129,128 | 12/1978 | McFarlane | 128/133 |
| 4,170,993 | 10/1979 | Alvarez | 604/180 |
| 4,224,937 | 9/1980 | Gordon | 128/133 |
| 4,250,880 | 2/1981 | Gordon | 128/214 |
| 4,297,995 | 11/1981 | Golub | 128/DIG. 26 |
| 4,333,468 | 6/1982 | Geist | 128/348 |
| 4,366,817 | 1/1983 | Thomas | 604/174 |
| 4,392,856 | 7/1983 | Lichtenstein | 604/177 |
| 4,460,356 | 7/1984 | Moseley | 604/180 |
| 4,484,914 | 11/1984 | Brown | 604/180 |
| 4,563,177 | 1/1986 | Kamen | 604/177 |
| 4,698,057 | 10/1987 | Joishy | 604/180 |
| 4,710,176 | 12/1987 | Quick | 604/177 |
| 4,726,716 | 2/1988 | McGuire | 604/180 |
| 4,781,293 | 11/1988 | Johns | 206/441 |
| 4,820,282 | 4/1989 | Hogan | 604/263 |
| 4,822,342 | 4/1989 | Brawner | 604/180 |
| 4,828,529 | 5/1989 | Kualo | 604/164 |
| 4,915,227 | 4/1990 | Johns | 206/441 |
| 4,915,228 | 4/1990 | Johns | 206/441 |

FOREIGN PATENT DOCUMENTS 0145142  6/1985  European Pat. Off. ............ 604/179

Primary Examiner—John D. Yasko
Assistant Examiner—Anthony Gutowski
Attorney, Agent, or Firm—Robert R. Keegan; Daniel R. Alexander

[57] ABSTRACT

There is disclosed a catheter device with easily deployed retainer useful in securing medical appliances such as catheters, sensors, tubing, or the like, to a human or other patient. The device includes a catheter, or the like, with a self-adhesive tape which is attached and extends perpendicularly thereto. The self-adhesive tape may be a strip of conventional surgical or first aid adhesive tape and has each of its ends rolled towards the catheter in a scroll-like fashion; the tape preferably is pre-attached to the catheter by adhesive, heat sealing, or the like, and may have a medicine saturated pad on the bottom side to help prevent infection at the wound area. The adaptation of the device with any intravenous catheter does not change standard use in any way in relation to preparation of the site, or actual insertion of the catheter. After the vein has been accessed, the tape is simply unrolled by the thumb and index finger with moderate pressure to secure the catheter to the patient's skin. This allows the nurse or technician a free hand to prepare connection of tubing, or the like. Alternatively, the self-adhesive tape can be attached to the catheter by means of a stud which captures the tape by engaging a hole therein. The stud allows the tape to pivot and be positioned relative to the catheter in a somewhat oblique fashion. The stud or other fastener also allows one of several different sizes of tape to be attached immediately before use.

13 Claims, 2 Drawing Sheets

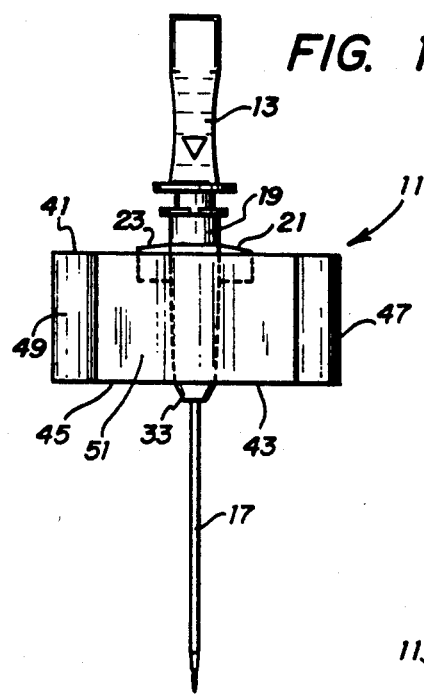
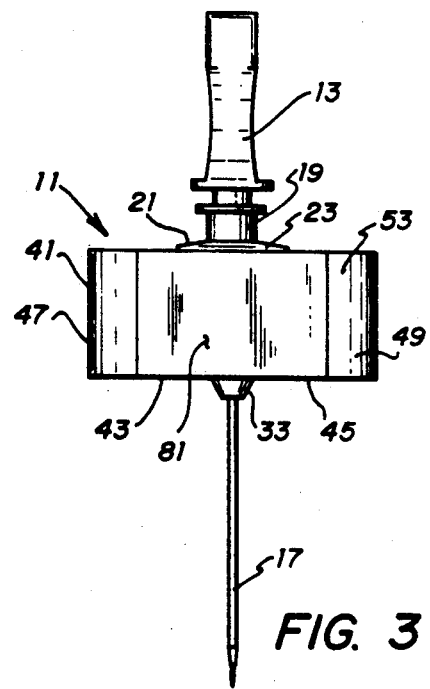
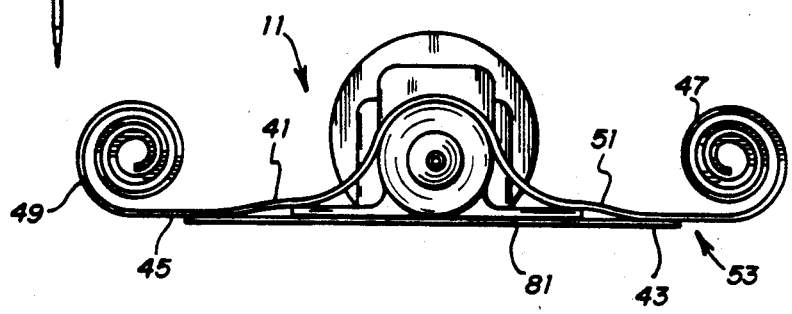
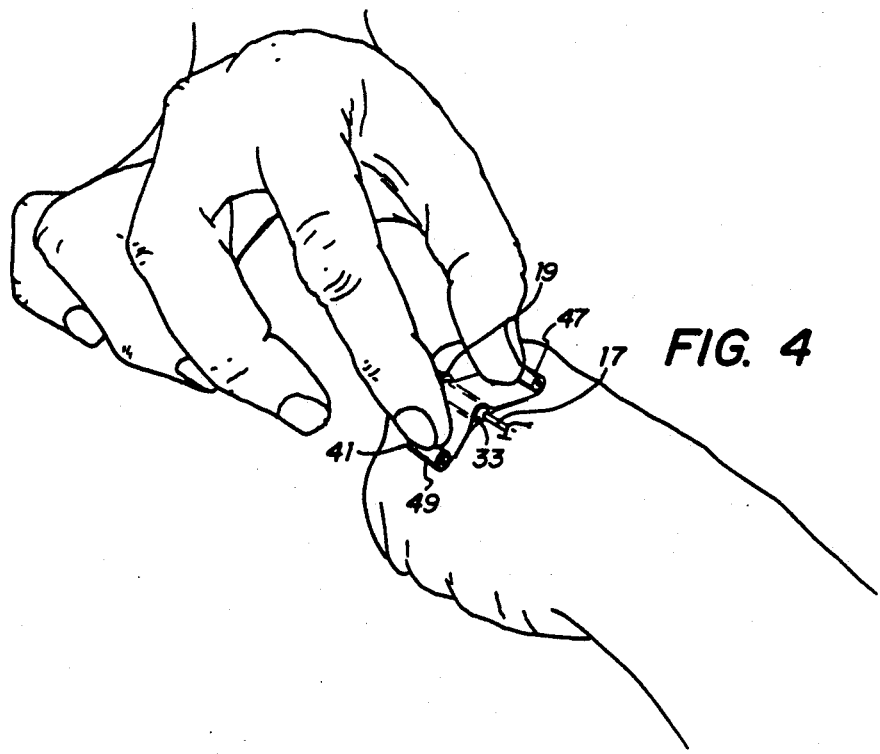

CATHETER DEVICE WITH EASILY DEPLOYED RETAINER

BACKGROUND OF THE INVENTION

This invention pertains to apparatus for retaining medical appliances such as catheters, sensors, tubing, or the like, to a patient (human or other animal). It has been common practice to use adhesive tape or the like to retain a medical appliance to the patient near the point of insertion of a catheter, for example.

Previous patented devices for retaining catheters, or the like, have employed self-adhesive fastening elements. U.S. Pat. No. 4,563,177 discloses such a device for stabilizing a catheter on a patient. It consists of a pair of flaps affixed to a patient's skin, and an central portion having a contour for receiving the catheter. The catheter is inserted into the patient then the catheter stabilization pad is used to retain the catheter to the patient. U.S. Pat. No. 4,822,342 uses a prepared tape with a pull tab to expose an adhesive surface of the tape to retain the catheter to a patient. U.S. Pat. No. 4,333,468 employs an apparatus that includes a base plate that is adhered to a patient's skin, and a flap to retain the medical device to the patient. U.S. Pat. Nos. 4,250,880 and 4,224,937 to Gordon disclose a stabilizing fitting for an intravenous catheter that is taped onto a patient after a catheter has been connected to it. The prior retaining devices are quite different from the present invention in that they require two hands to position the catheter and retaining device to the patient. The prior retaining devices also require then to be attached to the catheter after it has been inserted. In the present invention the means to retain the catheter to the patient may be integrally attached to the catheter, thereby allowing quicker and easier fastening to the patient.

SUMMARY OF THE INVENTION

A standard practice in the medical field for applying a catheter is to prepare several strips of tape and place them on the edge of a table or bed rail. The nurse or technician inserts the catheter into the patient. While holding the catheter in place, the nurse or technician retrieves and applies the tape to retain the catheter to the patient. This process is very cumbersome and may lead to great discomfort for the patient. It also subjects the patient to an increased risk of contamination. The present invention eliminates this awkward procedure. Since the nurse or technician will have a free hand, the catheter, or the like, may be retained more easily. This allows for greater control of a confused, young, combative, or elderly patient or one unable to remain still for this delicate procedure. It also allows the nurse or technician to perform some function with the other hand at the same time that the catheter is being retained. The present invention can also be modified to have a stud that allows the scroll tape to be engaged at a medial slot therein and pivotally positioned with one hand. This gives greater flexibility to how the catheter is retained. Such a stud may also allow the scroll tape to be snapped onto the catheter, or the like. This allows the nurse or technician to choose what size of tape to use.

In addition to providing the above described features and advantages, it is an object of the present invention to provide means for retaining a catheter or the like to a patient using one hand. The catheter can be inserted and retained while the other hand is left to hold the patient, or to perform some other function.

It is another object of the present invention to have a means integral with the catheter for retaining a catheter, or the like, to a patient wherein such retaining device is pre-attached to the catheter, or the like, and does not require the person who is retaining the device to the patient to attach the device to the catheter.

It is another object of the present invention to eliminate the steps that a nurse or technician would have to take to prepare the retaining device for use.

It is another object of the present invention to reduce handling of the retaining device, so as to offer a more sterile retaining device.

It is another object of the present invention to simplify the use of catheters, or the like, since the retaining device may be included with the catheter, thus reducing the storage and the need for maintaining availability of the catheters and the separate retaining devices.

It is still another object of the present invention to provide a means for retaining an appliance with an easily deployed retainer which has been pre-attached while using only one hand.

BRIEF DESCRIPTION OF THE DRAWINGS

FIG. 1 is a top plan view of a catheter with a retaining device in a non-extended state;

FIG. 2 is a front elevational view thereof;

FIG. 3 is a bottom plan view thereof;

FIG. 4 is a perspective view of the catheter of FIGS. 1 through 3 being retained by use of the retaining device;

DESCRIPTION OF THE PREFERRED EMBODIMENT

Figure 5:
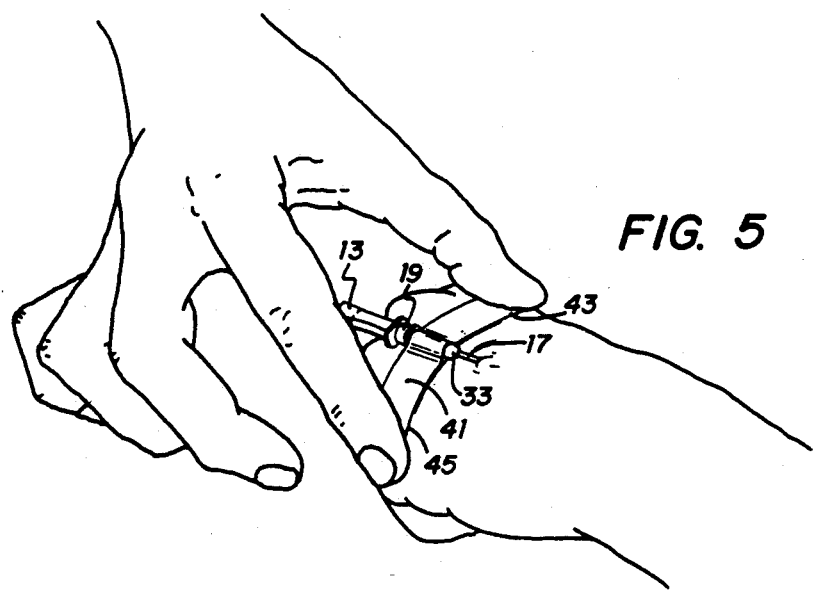
FIG. 5 is a perspective view of the catheter of FIGS. 1 through 3 with the retaining device fully extended.

Referring now to the drawings, and particularly to FIG. 1 and FIG. 2 (showing a preferred embodiment of this invention), an easily deployed retaining device 11 is provided for a catheter 13 which is commonly used in the medical profession. The catheter 13 consists of a needle 17 that is attached to catheter body 19 at catheter hub 33. At the opposite end from catheter hub 33, catheter body 19 has two ears 21 and 23 that extend outwardly.

Catheter 13 with retaining device 11 has a self-adhesive tape 41 with scrolled ends 47 and 49 that is joined at about its midpoint perpendicularly to catheter 13. The self-adhesive tape 41 is namely a strip of conventional surgical adhesive tape, but any tape with similar tackiness will do. The self-adhesive tape 41 preferably has a non-adhesive surface 51 and a self-adhesive surface 53. The tape 41 is typically about one-half inch wide and three inches long (when unrolled). The length and width of the tape 41 can vary depending upon the size of the catheter 13, or of the area to which it is being retained. The tape 41 may be attached to catheter 13 perpendicularly to catheter body 19 between the two ears (21 and 23), and catheter hub 33. The tape 41 has its two halves 43 and 45 at least partially rolled with two windings towards the catheter body 19 to form scrolled ends 47 and 49. The catheter retaining device 11 is preferably supplied to the user with the catheter 13 and the self-adhesive tape 41 permanently joined or pre-attached.

Referring now to FIG. 4 and FIG. 5, the catheter 13 is grasped by one hand at catheter body 19 and the needle 17 is inserted up to catheter hub 33.

The procedure for use of the adaptation of the present invention to any intravenous catheter does not change standard use in any way in relation to preparation of the site or actual insertion of the catheter. After the vein has been accessed, the tape 11 is simply unrolled at scrolled ends 47 and 49 by the thumb and index finger of one hand with moderate pressure to retain the catheter 13 to the patient's skin. This allows the nurse or technician a free hand to prepare connection of tubing or lock. This also prevents the nurse from having to prepare several strips of tape and possible contamination of the tape on the edge of the table or bed rail. The catheter 13 can then be retained further with any dressing which the individual institution considers necessary for infection control.

In the preferred embodiment, the tape 41 is pre-attached by adhesive, heat-sealing, or the like, to catheter 13 thereby eliminating the need for the nurse or technician using the catheter 13 with retaining device 11 to assemble it before use.

Figure 6:
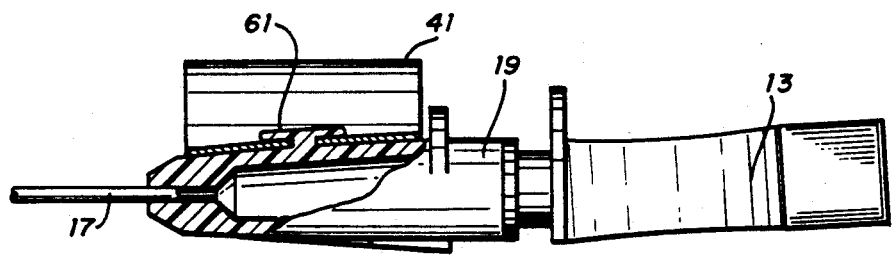
FIG. 6 is a side cross-sectional view showing a modified form of the catheter with retaining device that has a stud for attaching the slotted retaining device to the catheter.
Figure 7:
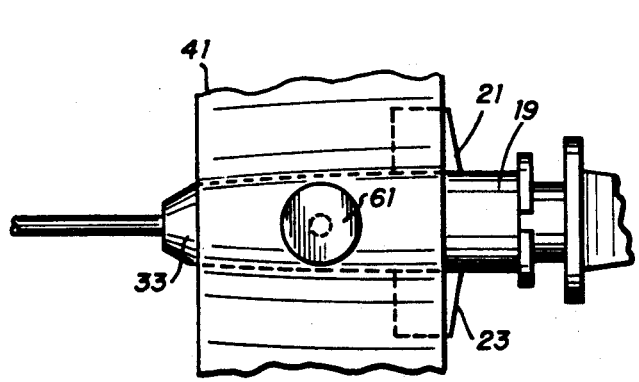
FIG. 7 is a top plan view thereof.

An alternative method for retaining adhesive tape 41 to catheter body 19 is by means of a stud 61 as shown in FIGS. 6 and 7. Stud 61 captures tape 41 by engaging a slot provided therein, and retains it to catheter body 19. The stud 61 may allow the tape 41 to pivot in a horizontal plane, this allows the tape 41 to be retained in an oblique fashion instead of perpendicular to catheter body 19.

The stud 61 may also allow a tape 41 to be selected and attached right before use. The stud 61 could also be made up of a snap or similar device with the male part of the stud permanently affixed to the catheter body 19 and the female part of the snap would be affixed to the tape 41.

Figure 8:
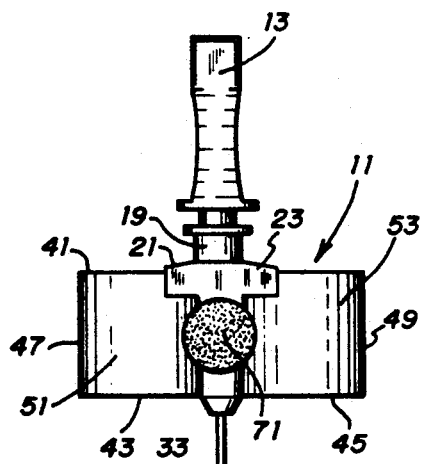
FIG. 8 shows an alternative embodiment similar to that of FIG. 3 with a sterile absorbent pad.
Figure 9:
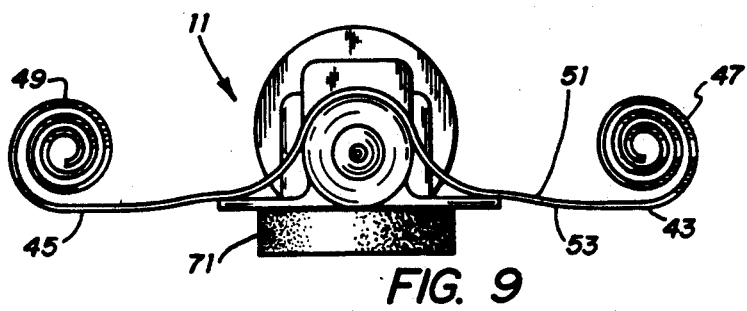
FIG. 9 shows an alternative embodiment similar to that of FIG. 2 with a sterile absorbent pad of FIG. 8.

Another embodiment of the invention includes a sterilized absorbent pad 71 as shown in FIGS. 8 and 9 which is attached to the bottom of catheter body 19 next to catheter hub 33. The sterile absorbent pad 71 will assist in preventing infection at the point of insertion of needle 17. The sterile absorbent pad 71 is about three-eighths of an inch in diameter and one-eighth inch thick. Sterile absorbent pad 71 may be treated with an antiseptic and/or antibiotic to further prevent the possibility of infection. This offers not only a physical barrier to infection, but also a sterilizing agent.

Referring to FIG. 3, the self-adhesive tape 41 may have a separate bottom tape 81 that extends from side 43 to side 45. Each face of bottom tape 81 preferably will have an adhesive surface. One face of the bottom tape 81 will be retained to the bottom of catheter body 19. This helps retain tape 41 to the catheter 13. The opposite face of bottom tape 81 will help retain catheter 13 to the patient.

Retaining devices according to this invention can be used with a variety of items. It can be used with all sorts of medical devices to retain them in human or animal use. It also has application in non-medical fields whenever an item is desired to be retained using one hand. The tape 41 can be pre-attached to the item thereby allowing the item to be retained using just one hand.

In addition to the variations and modifications to the invention which have been described, shown or suggested, other variations and modifications to the invention will be apparent to those skilled in the art, and, accordingly, the scope of the invention is not to be considered limited to the particular embodiments and variations thereof shown or suggested, but is rather to be determined by reference to the appended claims.

What is claimed is:

1. Apparatus in the form of a catheter body with associated means for retaining it in operative position on a patient comprising:
    a catheter body;
    an elongated flexible tape with a pressure sensitive adhesive on one surface thereof, and a non-adhesive portion on the opposite surface;
    said flexible tape having each of its opposite ends rolled adhesive surface outwardly towards the mid-point of said flexible tape;
    means integral with said body for attaching said flexible tape near its mid-point transversely to said catheter body;
    an absorbent pad secured on the underside of said catheter body; and
    whereby said catheter body can be secured in operative position on a patient with the thumb and a finger of one hand.

2. Apparatus as recited in claim 1 wherein said means for attaching said flexible tape to said catheter body comprises an adhesive.

3. Apparatus as recited in claim 1 wherein said flexible tape is at least three inches long.

4. Apparatus as recited in claim 3 wherein said flexible tape is at least one-quarter inch in width.

5. Apparatus as recited in claim 1 wherein said means for attaching further includes a second tape secured to the underside of said catheter body.

6. Apparatus in the form of a catheter body with associated means for retaining it in operative position on a patient comprising:
    a catheter body;
    an elongated flexible tape with a pressure sensitive adhesive on one surface thereof, and a non-adhesive portion on the opposite surface;
    said flexible tape having each of its opposite ends rolled adhesive surface outwardly towards the mid-point of said flexible tape;
    means integral with said body for attaching said flexible tape near its mid-point transversely to said catheter body;
    wherein said means for attaching said flexible tape to said catheter body further comprises a second tape secured on the underside of said catheter body; and
    whereby said catheter body can be secured in operative position on a patient with the thumb and a finger of one hand.

7. Apparatus as recited in claim 6 further comprising an absorbent pad secured on the underside of said catheter body.

8. Apparatus as recited in claim 6 wherein said means for attaching said flexible tape to said catheter body comprises an adhesive.

9. Apparatus in the form of a catheter body with associated means for retaining it in operative position on a patient comprising:
    a catheter body an elongated flexible tape with a pressure sensitive adhesive on one surface thereof, and a non-adhesive portion on the opposite surface.

said flexible tape having each of its opposite ends rolled adhesive surface outwardly towards the mid-point of said flexible tape;

means integral with said body for attaching said flexible tape near its mid-point transversely to said catheter body;

wherein said flexible tape has an opening near its mid-point and said means for attaching said flexible tape to said catheter body is a stud adapted to engage said opening in said tape; and whereby said catheter body can be secured in operative position on a patient with the thumb and a finger of one hand.

10. Apparatus as recited in claim 9 wherein said stud pivotally connects said flexible tape to said catheter body.

11. A clinical catheter-to-patient attachment apparatus for a catheter having a body and extending ears comprising:

a top elongated flexible tape at least twice as wide as the ears of the catheter and at least as long as wide with a pressure sensitive adhesive on one surface thereof, and a non-adhesive surface on the opposite side thereof;

said top elongated flexible tape having its opposite ends rolled towards the mid-point of said elongated flexible tape.

a bottom elongated flexible tape of about the same width as said top elongated flexible tape and a length at least about the width of the catheter body with a pressure sensitive adhesive on at least one surface thereof; and said top and bottom elongated flexible tapes being attached together and to said catheter at about the mid-point of said top and bottom elongated flexible tapes, whereby said catheter can be secured to the patient with the thumb and finger of one hand.

12. Apparatus as recited in claim 11 wherein said elongated flexible tapes are attached to said catheter by an adhesive.

13. Apparatus as recited in claim 11 further including an absorbent pad secured on the lower surface of said bottom elongated flexible tape.

* * * * *